United States Patent [19]

Stroech et al.

[11] Patent Number: 4,925,482
[45] Date of Patent: May 15, 1990

[54] FUNGICIDAL AND PLANT GROWTH-REGULATING HYDROXYALKYL-AZOLYL DERIVATIVES

[75] Inventors: Klaus Stroech, Solingen; Monika Frie, Odenthal; Thomas Himmler, Cologne; Wilhelm Brandes, Leichlingen; Stefan Dutzmann, Duesseldorf; Gerd Hänssler, Leverkusen, all of Fed. Rep. of Germany

[73] Assignee: Bayer Aktiengesellschaft, Leverkusen, Fed. Rep. of Germany

[21] Appl. No.: 216,690

[22] Filed: Jul. 7, 1988

[30] Foreign Application Priority Data

Jul. 10, 1987 [DE] Fed. Rep. of Germany ....... 3722794
Apr. 25, 1988 [DE] Fed. Rep. of Germany ....... 3813874

[51] Int. Cl.$^5$ ............... A01N 43/653; C07D 249/08
[52] U.S. Cl. ........................................ 71/92; 71/76; 514/184; 514/383; 548/101; 548/266; 548/4; 548/267.8
[58] Field of Search ............... 548/101, 262; 514/383, 514/184; 71/76, 92

[56] References Cited

U.S. PATENT DOCUMENTS

| | | | |
|---|---|---|---|
| 4,548,945 | 10/1985 | Holmwood et al. | 514/383 |
| 4,723,984 | 2/1988 | Holmwood et al. | 71/76 |

FOREIGN PATENT DOCUMENTS

| | | | |
|---|---|---|---|
| 0052424 | 5/1982 | European Pat. Off. | |
| 0143379 | 6/1985 | European Pat. Off. | |
| 0143384 | 6/1985 | European Pat. Off. | |
| 0180136 | 5/1988 | European Pat. Off. | |
| 2129000 | 5/1984 | United Kingdom | 548/262 |

OTHER PUBLICATIONS

Chemical Abstracts, vol. 77, No. 18, p. 324, Abstract 125650h.
Chemical Abstracts, vol. 86, No. 7, p. 494, Abstract 43227x.
Chemical Abstracts, vol. 92, No. 3, p. 648, Abstract 22100j.

Primary Examiner—Richard L. Raymond
Assistant Examiner—Patricia L. Morris
Attorney, Agent, or Firm—Sprung, Horn, Kramer & Woods

[57] ABSTRACT

Fungicidal and plant growth-regulating hydroxyalkylazolyl derivatives of the formula

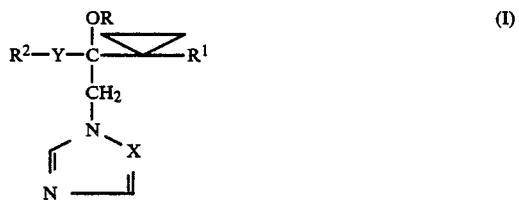

in which
R represents hydrogen, alkyl or acyl,
$R^1$ represents halogen, optionally substituted phenyl or the grouping -Z-$R^3$, wherein
  Z represents oxygen, sulphur, SO or $SO_2$ and
  $R^3$ represents optionally substituted alkyl, optionally substituted phenyl or optionally substituted phenylalkyl,
$R^2$ represents optionally substituted alkyl, optionally substituted cycloalkyl, optionally substituted naphthyl or the radical of the formula

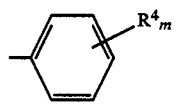

m represents the numbers 0, 1, 2 or 3, or
$R^2$ represents the radical or the formula

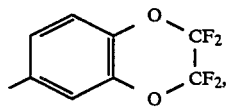

X represents nitrogen or a CH group and
Y represents the groupings -$CH_2$-$CH_2$-, -CH=CH-, -C≡C-,

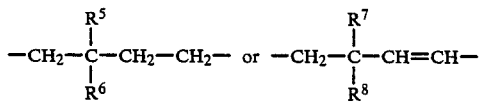

and their addition products with acids and metal salts.

13 Claims, No Drawings

FUNGICIDAL AND PLANT GROWTH-REGULATING HYDROXYALKYL-AZOLYL DERIVATIVES

The present invention relates to new hydroxyalkylazolyl derivatives, several processes for their preparation and their use as fungicides and plant growth regulators.

It has already been disclosed that numerous hydroxyalkyl-azolyl derivatives possess fungicidal and plant growth regulating properties (compare EP-OS (European Published Specification) 0,040,345 and EP-OS (European Published Specification) 0,052,424). The activity of these substances is very good; however, in some cases the activity leaves something to be desired at low dose rates.

New hydroxyalkyl-azolyl derivatives of the formula

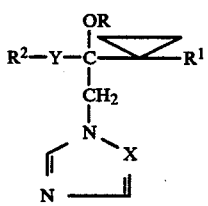  (I)

in which
R represents hydrogen, alkyl or acyl,
R$^1$ represents halogen, optionally substituted phenyl of the grouping —Z—R$^3$, wherein
  Z represents oxygen, sulphur, SO or SO$_2$ and
  R$^3$ represents optionally substituted alkyl, optionally substituted phenyl or optionally substituted phenylalkyl,
R$^2$ represents optionally substituted alkyl, optionally substituted cycloalkyl, optionally substituted naphthyl or the radical of the formula

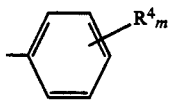

wherein
R$^4$ represents halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 halogen atoms, halogenoalkoxy having 1 or 2 carbon atoms and 1 to 5 halogen atoms, halogenoalkylthio having 1 or 2 carbon atoms and 1 to 5 halogen atoms, phenyl, whichis optionally substituted by alkyl having 1 or 2 carbon atoms and/or halogenk, phenoxy, which is optionally substituted by alkyl having 1 or 2 carbon atoms and/or halogen, nitro, amino, alkylamino, dialkylamino, arylamino or alkylcarbonylamino and
m represents the numbers 0, 1, 2 or 3, or
R$^2$ represents the radical or the formula

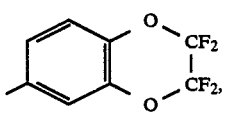

X represents nitrogen or a CH group and
Y represents the groupings —CH$_2$—CH$_2$—, —CH=CH—, —C≡C—,

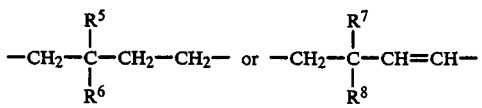

wherein
R$^5$, R$^6$, R$^7$ und R$^8$ independently of one another represent hydrogen or alkyl having 1 to 4 carbon atoms, and their acid addition salts and metal salt complexes, have now been found.

The substances according to the invention contain an asymmetrically substituted carbon atom. They can therefore occur in optically isomeric forms. Moreover, those substances of the formula (I) in which Y represents a —CH=CH— group or a

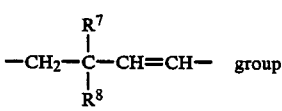 group can also exist in the form of cis or trans isomers. The invention relates both to the individual isomers and to their mixtures.

Furthermore, it has been found that hydroxyalkylazolyl derivatives of the formula (I) and their acid addition salts and metal salt complexes are obtained when (a) oxiranes of the formula

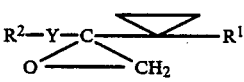  (II)

in which
R$^1$, R$^2$ and Y have the abovementioned meaning, are reacted with azoles of the formula

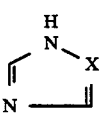

in which
X has the abovementioned meaning, in the presence of acid-binding agent and in the presence of a diluent, or (b) hydroxyalkyl-azolyl-derivatives of the formula

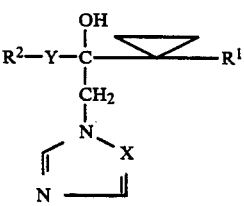  (Ia)

in which
R$^1$, R$^2$, X and Y have the abovementioned meaning, are reacted with strong bases in the presence of a diluent and the alcoholates of the formula

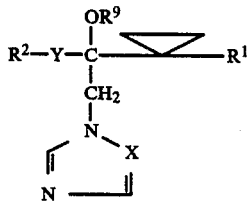 (Ib)

in which
R$^1$, R$^2$, X and Y have the abovementioned meaning and

R$^9$ represents a cationic radical of a base, produced in this reaction are reacted with halogen compounds of the formula

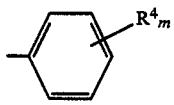 (IV)

in which
R$^{10}$ represents alkyl or acyl and
Hal represents halogen,
in the presence of a diluent, and subsequently, if desired, an acid or a metal salt is added to the compounds of the formula (I) thus obtained to form the acid addition salt or metal salt complex.

Finally, it has been found that the new hydroxyalkylazolyl derivatives of the formula (I) and their acid addition salts and metal salt complexes possess strong fungicidal and plant growth regulating properties.

Surprisingly, the substances according to the invention show a better fungicidal and plant growth regulating activity than the previously known compounds which resemble these most closely in terms of structure with an equivalent type of action.

Formula (I) provides a general definition of the hydroxyalkyl-azolyl derivatives according to the invention. Preferably, in this formula R represents hydrogen, alkyl having 1 to 6 carbon atoms or alkylcarbonyl having 1 to 6 carbon atoms in the alkyl part, R$^1$ represents fluorine, chlorine, bromine, phenyl which is optionally substituted by halogen, halogenoalkyl having 1 or 2 carbon atoms and 1 to 5 halogen atoms, alkyl having 1 to 4 carbon atoms and/or alkoxy having 1 to 4 carbon atoms, or the grouping —Z—R$^3$, wherein Z represents oxygen, sulphur, SO or SO$_2$ and
R$^3$ represents alkyl having 1 to 6 carbon atoms, which is optionally substituted by alkoxy having 1 to 4 carbon atoms, alkylthio having 1 to 4 carbon atoms, phenyl and/or halogen; or phenyl which is optionally substituted by halogen, halogenoalkyl having 1 or 2 carbon atoms and 1 to 5 halogen atoms, alkyl having 1 to 4 carbon atoms and/or alkoxy having 1 to 4 carbon atoms, or benzyl which is optionally substituted in the phenyl part by halogen, halogenoalkyl having 1 or 2 carbon atoms and 1 to 5 halogen atoms, alkyl having 1 to 4 carbon atoms and/or alkoxy having 1 to 4 carbon atoms, R$^2$ represents alkyl having 1 to 6 carbon atoms, which is optionally substituted by alkoxy having 1 to 4 carbon atoms, alkylthio having 1 to 4 carbon atoms, phenyl and/or halogen; cycloalkyl having 3 to 8 carbon atoms, which is optionally substituted by alkyl having 1 to 4 carbon atoms and/or halogen; naphthyl which is optionally substituted by alkyl having 1 to 4 carbon atoms and/or halogen; or the radical of the formula

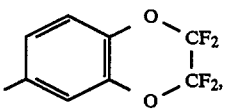

wherein
R$^4$ represents fluorine, chlorine, bromine, methyl, ethyl, isopropyl, tert,-butyl, methoxy, methylthio, trifluoromethyl, trifluoromethoxy, trifluoromethylthio, phenyl which is optionally substituted by fluorine, chlorine and/or methyl, phenoxy which is optionally substituted by fluorine, chlorine and/or methyl, or nitro, amino, alkylamino having 1 to 4 carbon atoms in the alkyl group, dialkylamino having 1 to 4 carbon atoms in each alkyl group, phenylamino or alkylcarbonylamino having 1 to 4 carbon atoms in the alkyl group and
m represents the numbers 0, 1, 2 or 3, or
R$^2$ represents the radical of the formula

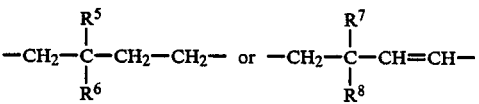

X represents nitrogen or a CH group and
Y represents the groupings —CH$_2$—CH$_2$—, CH=CH—, —C≡C—, $$—CH_2—\underset{R^6}{\overset{R^5}{C}}—CH_2—CH_2— \text{ or } —CH_2—\underset{R^8}{\overset{R^7}{C}}—CH=CH—$$

wherein
R$^5$, R$^6$, R$^7$ and R$^8$ independently of one another represent hydrogen, methyl or ethyl, When m represents the numbers 2 or 3, the radicals representing R$^4$ can be identical or different.

Particularly preferred compounds are those of the formula (I) in which

R represents hydrogen, methyl, ethyl, n-propyl, isopropyl, n-butyl, isobutyl, methylcarbonyl, ethylcarbonyl, n-propylcarbonyl, isopropylcarbonyl, n-butylcarbonyl and isobutylcarbonyl, R$^1$ represents fluorine, chlorine, bromine, phenyl which is optionally monosubstituted to trisubstituted by identical or different substituents from the series comprising fluorine, chlorine, bromine, trifluoromethyl, methyl, ethyl, methoxy and/or ethoxy, or the grouping of the formula —Z—R$^3$, wherein
Z represents oxygen, sulphur, SO or SO$_2$ and
R$^3$ represents methyl, ethyl, n-propyl, isopropyl, n-butyl, isobutyl or tert.-butyl, where each of these radicals can be monosubstituted to trisubstituted by identical or different substituents from the series comprising methoxy, ethoxy, methylthio, phenyl, fluorine, chlorine and/or bromine, or
R$^3$ represents phenyl which is optionally monosubstituted to trisubstituted by identical or different substituents from the series comprising fluorine, chlorine, bromine, trifluoromethyl, methyl, ethyl, methoxy and/or ethoxy or $R^3$ represents benzyl which can be optionally monosubstituted to trisubstituted in the phenyl part by identical or different substituents from the series comprising fluorine, chlorine, bromine, trifluoromethyl, methyl, ethyl, methoxy and/or ethoxy, $R^2$ represents alkyl having 1 to 4 carbon atoms, which is optionally monosubstituted to trisubstituted by identical or different substituents from the series comprising methoxy, ethoxy, methylthio, ethylthio, phenyl, fluorine, chlorine and/or bromine, and furthermore cycloalkyl having 3 to 7 carbon atoms, which is optionally monosubstituted to trisubstituted by identical or different substituents from the series comprising methyl, ethyl, fluorine and/or chlorine, and additionally naphthyl which is optionally monosubstituted to trisubstituted by identical or different substituents from the series comprising methyl, fluorine and/or chlorine, or the radical of the formula

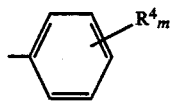

wherein $R^4$ represents fluorine, chlorine, bromine, methyl, ethyl, isopropyl, tert.-butyl, methoxy, methylthio, trifluoromethyl, trifluoromethoxy, trifluoromethylthio, phenyl which is optionally substituted by fluorine, chlorine and/or methyl, or phenoxy which is optionally substituted by fluorine, chlorine and/or methyl, or nitro, amino, alkylamino having 1 or 2 carbon atoms in the alkyl group, dialkylamino having 1 or 2 carbon atoms in each alkyl group, phenylamino or alkylcarbonylamino having 1 or 2 carbon atoms in the alkyl group, m represents the numbers 0, 1, 2 or 3, or $R^2$ represents the radical of the formula

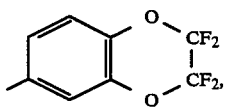

X represents nitrogen or a CH group and

Y represents the groupings —CH$_2$—CH$_2$—, —CH=CH, C≡C—,

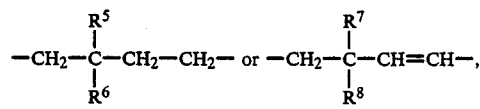

wherein $R^5$, $R^6$, $R^7$ and $R^8$ independently of one another represent hydrogen, methyl or ethyl.

Preferred compounds according to the invention are also addition products of acids and those hydroxyalkylazolyl derivatives of the formula (I) in which R, $R^1$, $R^2$, X and Y have the meanings which have already been mentioned as preferable for these radicals.

The acids which can be added to form acid addition salts preferably include hydrohalic acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic and lactic acid and also sulphonic acids, such as, for example, p-toluenesulphonic acid, 1,5-naphthalenedisulphonic acid or camphorsulphonic acid.

In addition, preferred compounds according to the invention are addition products of salts of metals of main groups II to IV and subgroups I and II and also IV to VIII of the periodic table of the elements and those hydroxyalkyl-azolyl derivatives of the formula (I) in which R, $R^1$, $R^2$, X and Y have the meanings which have already been mentioned as preferable for these radicals.

Salts of copper, zinc, manganese, magnesium, tin, iron and nickel are particularly preferred here. Possible anions of these salts are those which are derived from those acids which result in physiologically acceptable addition products.

In this connection, particularly preferred acids of this type are hydrohalic acids, such as, for example, hydrochloric acid and hydrobromic acid, and furthermore phosphoric acid, nitric acid and sulphuric acid.

The substances shown in the following tables may be mentioned as examples of hydroxyalkyl-azolyl derivatives of the formula (I):

TABLE 1

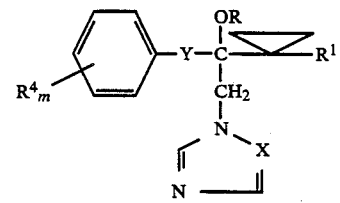

(Ic)

| $R^4_m$ | R | X | $R^1$ | Y |
|---|---|---|---|---|
| 2,4-Cl$_2$ | H | N | Cl | —CH$_2$—CH$_2$— |
| 2,4-F$_2$ | H | N | Cl | " |
| 4-CH$_3$ | H | N | Cl | " |
| 4-CF$_3$ | H | N | Cl | " |
| 4-OCF$_3$ | H | N | Cl | " |
| 4-OCH$_3$ | H | N | Cl | " |
| 4-SCH$_3$ | H | N | Cl | " |
| 3-Cl | H | N | —S—CH$_3$ | " |

TABLE 1-continued
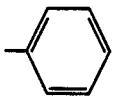
(Ic)
| $R^4{}_m$ | R | X | $R^1$ | Y |
|---|---|---|---|---|
| 4-Cl | H | N | —S—$C_2H_5$ | " |
| 2,3,6-$Cl_3$ | " | " | Cl | —$CH_2$—$CH_2$— |
| 4-Cl | " | " | F | " |
| 4-Cl | " | CH | Cl | " |
| 4-Cl | $CH_3$ | N | Cl | " |
| 4-Cl | H | " | 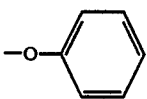 | " |
| 4-Cl | " | " | 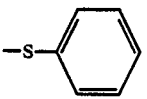 | " |
| 4-Cl | " | " | 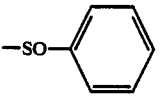 | " |
| 4-Cl | " | " | 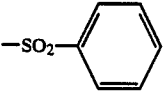 | " |
| 4-Cl | " | " | 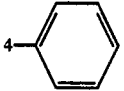 | " |
| 4-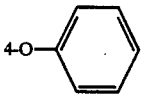 | " | " | Cl | " |
| 4-O-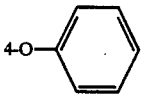 | " | " | Cl | " |
| 4-t.-$C_4H_9$ | " | " | Cl | " |
| 2-Cl, 4-$CH_3$ | " | " | Cl | " |
| — | " | " | Cl | " |
| 4-Cl | —CO—$CH_3$ | " | Cl | " |
| 4-Cl | —$C_2H_5$ | " | Cl | " |
| 4-F | $CH_3$ | " | F | " |
| 2,4-$Cl_2$ | H | N | Cl | —CH=CH— |
| 2,4-$F_2$ | H | N | Cl | " |
| 4-$CH_3$ | H | N | Cl | " |
| 4-$CF_3$ | H | N | Cl | " |
| 4-$OCF_3$ | H | N | Cl | " |
| 4-$OCH_3$ | H | N | Cl | " |
| 4-$SCH_3$ | H | N | Cl | " |
| 3-Cl | H | N | —S—$CH_3$ | " |
| 4-Cl | H | N | —S—$C_2H_5$ | " |
| 2,4,6-$Cl_3$ | " | " | Cl | —CH=CH— |
| 4-Cl | " | " | F | " |
| 4-Cl | " | CH | Cl | " |
| 4-Cl | $CH_3$ | N | Cl | " |

TABLE 1-continued
(Ic)
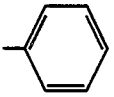
| $R^4_m$ | R | X | $R^1$ | Y |
|---|---|---|---|---|
| 4-Cl | H | " | 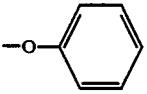 | " |
| 4-Cl | " | " | —O-⌬ | " |
| 4-Cl | " | " | —S-⌬ | " |
| 4-Cl | " | " | —SO-⌬ | " |
| 4-Cl | " | " | —SO$_2$-⌬ | " |
| 4-⌬ | " | " | Cl | " |
| 4-O-⌬ | " | " | Cl | " |
| 4-t.-C$_4$H$_9$ | " | " | Cl | " |
| 2-Cl, 4-CH$_3$ | " | " | Cl | " |
| — | " | " | Cl | " |
| 4-Cl | —CO—CH$_3$ | " | Cl | " |
| 4-Cl | —C$_2$H$_5$ | " | Cl | " |
| 4-F | CH$_3$ | " | F | " |
| 2,4-Cl$_2$ | H | N | Cl | —C≡C— |
| 2,4-F$_2$ | H | N | Cl | " |
| 4-CH$_3$ | H | N | Cl | " |
| 4-CF$_3$ | H | N | Cl | " |
| 4-OCF$_3$ | H | N | Cl | " |
| 4-OCH$_3$ | H | N | Cl | " |
| 4-SCH$_3$ | H | N | Cl | " |
| 3-Cl | H | N | —S—CH$_3$ | " |
| 4-Cl | H | N | —S—C$_2$H$_5$ | " |
| 2,4,6-Cl$_3$ | " | " | Cl | —C≡C— |
| 4-Cl | " | " | F | " |
| 4-Cl | " | CH | Cl | " |
| 4-Cl | CH$_3$ | N | Cl | " |
| 4-Cl | H | " | 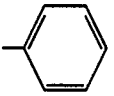 | " |

TABLE 1-continued
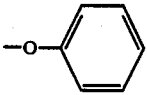
(Ic)
| $R^4_m$ | R | X | $R^1$ | Y |
|---|---|---|---|---|
| 4-Cl | " | " | -O-C₆H₅ (phenoxy) | " |
| 4-Cl | " | " | -S-C₆H₅ | " |
| 4-Cl | " | " | -SO-C₆H₅ | " |
| 4-Cl | " | " | -SO₂-C₆H₅ | " |
| 4-C₆H₅ (phenyl) | " | " | Cl | " |
| 4-O-C₆H₅ (phenoxy) | " | " | Cl | " |
| 4-t.-C₄H₉ | " | " | Cl | " |
| 2-Cl, 4-CH₃ | " | " | Cl | " |
| — | " | " | Cl | " |
| 4-Cl | —CO—CH₃ | " | Cl | " |
| 4-Cl | —C₂H₅ | " | Cl | " |
| 4-F | CH₃ | " | F | " |
TABLE 2
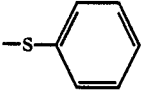
(I)
| $R^2$ | R | X | $R^1$ | Y |
|---|---|---|---|---|
| (CH₃)₃C— | H | N | Cl | —CH₂—CH₂— |
| FCH₂—C(CH₃)₂— | H | N | Cl | —CH₂—CH₂— |
TABLE 2-continued
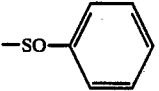
(I)
| $R^2$ | R | X | $R^1$ | Y |
|---|---|---|---|---|
| cyclohexyl | H | N | Cl | —CH₂—CH₂— |
| 1-methylcyclohexyl | H | N | Cl | —CH₂—CH₂— |

TABLE 2-continued

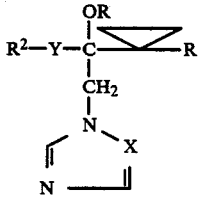

| R² | R | X | R¹ | Y |
|---|---|---|---|---|
| 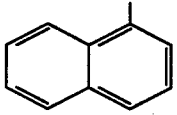 | H | N | Cl | —CH₂—CH₂— |
| 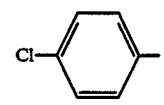 | H | N | Cl | —CH₂—C(CH₃)₂—CH₂—CH₂— |
| 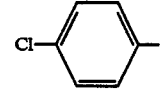 | H | N | Cl | —CH₂—C(CH₃)₂—CH=CH— |
| 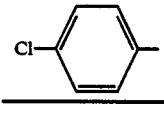 | H | N | Cl | —CH₂—CH₂—CH=CH— |

If 2-(1-chlorocyclopropyl)-2-(4-chlorophenylethyl)oxirane and 1,2,4-triazole are used as starting materials, then the course of process (a) according to the invention can be illustrated by the following equation:

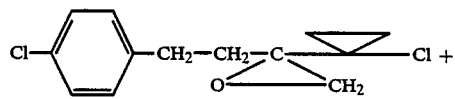

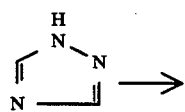

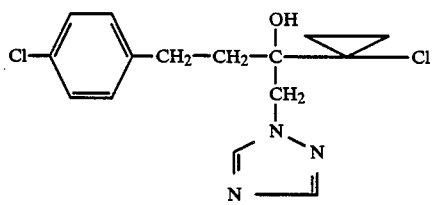

If 2-(1-chlorocyclopropyl)-4-(4-chlorophenyl)-1-(1,2,4-triazol-1-yl)-butan-2-ol and sodium hydride are used as starting materials and iodomethane as reaction component, then the course of process (b) according to the invention can be illustrated by the following equation:

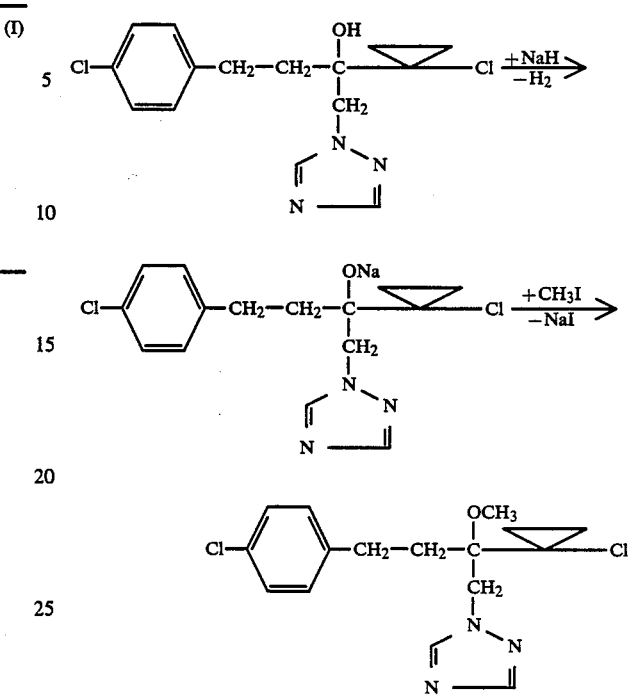

Formula (II) provides a general definition of the oxiranes required as starting materials for process (a) according to the invention. In this formula, $R^1$, $R^2$ and Y preferably have those meanings which have already been mentioned as preferable for these radicals in connection with the description of the substances of the formula (I) according to the invention.

The oxiranes of the formula (II) were hitherto unknown. They can be prepared by reacting (c) cyclopropyl ketones of the formula

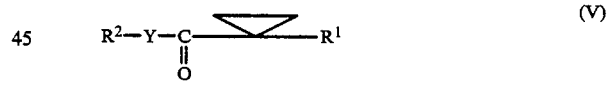

in which $R^1$, $R^2$ and Y have the abovementioned meaning, either with (α) dimethyloxosulphonium methylide of the formula

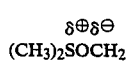

(VI)

or (β) dimethylsulphonium methylide of the formula

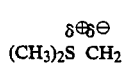

(VII)

in the presence of a diluent or by reacting (d) carbinols of the formula

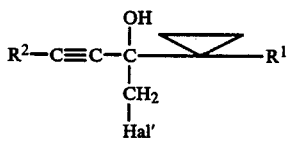 (VIII)

in which

R¹ and R² have the abovementioned meaning and

Hal' represents chlorine or bromine, with bases in the presence of a diluent.

The cyclopropyl ketones of the formula (V) required as starting materials for carrying out process (c) were hitherto unknown. They can be prepared by reacting (e) aldehydes of the formulae

 (IX-a)

or

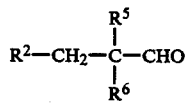 (IX-b)

in which

R², R⁵ and R⁶ have the abovementioned meaning, with methylcyclopropyl ketones of the formula

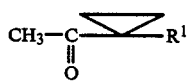 (X)

in which

R¹ has the abovementioned meaning, in the presence of a catalyst and in the presence of a diluent and if appropriate hydrogenating the cyclopropyl ketones of the formulae

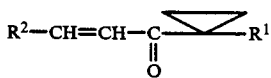 (V-a)

or

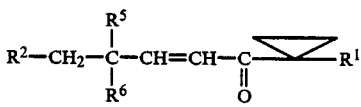 (V-b)

in which

R¹, R², R⁵ and R⁶ have the abovementioned meaning, produced in this reaction in the presence of a catalyst and in the presence of a diluent, or by reacting (f) acetylenes of the formula

 (XI)

in which

R² has the abovementioned meaning, with acid halides of the formula

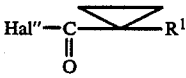 (XII)

in which

R¹ has the abovementioned meaning and

Hal" represents chlorine or bromine, in the presence of a catalyst and in the presence of a diluent.

The aldehydes of the formulae (IX-a) and (IX-b) required as starting materials in process (e) are generally known compounds of organic chemistry.

The methylcyclopropyl ketones of the formula (X) additionally required as reaction components for carrying out process (e) are known or can be prepared by processes which are known in principle (compare Synthesis 1977, 189).

Suitable catalysts for carrying out the first step of process (e) are all reaction accelerators customary for condensations of this type. Basic substances, for example alkali metal hydroxides, such as sodium hydroxide or potassium hydroxide are preferably utilizable.

For carrying out the first step of process (e), possible diluents are all inert organic solvents customary for reactions of this type. Alcohols, such as methanol, ethanol, isopropanol, n-butanol and tert.-butanol, are preferably utilizable.

The reaction temperatures can be varied within a relatively wide range when carrying out the first step of process (e). In general, the reaction is carried out at temperatures between 0° C. and 100° C., preferably between 10° C. and 80° C.

The first step of process (e) is normally carried out at atmospheric pressure. However, it is also possible to work at elevated or reduced pressure.

When carrying out the first step of process (e), 1 mole of aldehyde of the formula (IX) and also a catalytic amount of reaction accelerator are employed per mole of methylcyclopropyl ketone of the formula (X). However, it is also possible to use one component or the other in an excess. Working up takes place by customary methods. In general, a procedure is used in which the reaction products, which precipitates in solid state, are filtered off with suction and are used for further reactions, if necessary after previous purification.

In the second step of process (e), the cyclopropyl ketones of the formulae (V-a) or (V-b) are hydrogenated using hydrogen in the presence of a catalyst and a diluent. In this process, the reaction is carried out in the liquid phase using a suspended powdered hydrogenation catalyst (heterogeneous) or using a catalyst complex soluble in the diluent (homogeneous). The hydrogenation can be carried out discontinuously (batchwise) or continuously as a hydrogenation of the liquid-phase or trickle-bed type in known hydrogenation reactors, such as autoclaves, autoclave cascades, tube reactors or rotating reactors. The preferred procedure is discontinuous liquid-phase hydrogenation in the autoclave at elevated pressure.

Suitable diluents for carrying out the second step of process (e) are inert organic solvents. These preferably include alcohols, such as methanol, ethanol, isopropanol or ethylene glycol; ethers, such as diethyl ether, diisopropyl ether, ethylene glycol monomethyl ether, ethylene glycol dimethyl ether, dioxane or tetrahydrofuran, saturated hydrocarbons, such as n-heptane or cyclohexane; aromatic hydrocarbons, such as toluene; and also esters, such as ethyl acetate.

Suitable hydrogenation catalysts for the second step of process (e) are, for example, those which consist of metals and/or compounds of elements of the eighth subgroup of the periodic table of the elements according to Mendeleev or which contain these. The metals ruthenium, rhodium, palladium, platinum, cobalt and nickel and their compounds are preferred here. The metal compounds can be, for example, chlorides, oxides, hydroxides and/or oxihydrates.

The metals copper, vanadium, molybdenum, chromium and/or manganese, and also compounds of these metals, can additionally be present.

The hydrogenation catalysts can consist exclusively or preponderantly of hydrogen-transferring substances, but these can also be applied to support materials.

Suitable support materials for the hydrogentransferring substances are, for example: inorganic materials, such as kieselguhr, silica, aluminum oxide, alkali metal silicates and alkaline earth metal silicates, aluminium silicates, montmorillonite, zeolites, spinels, dolomite, kaolin, magnesium silicates, zirconium oxide, zinc oxide, calcium carbonate, silicon carbide, aluminium phosphate, boron phosphte, asbestos, activated charcoal or barium sulphate, and also organic materials, for example naturally occurring or synthetic compounds having high molecular weights such as silk, polyamides, polystyrenes, cellulose or polyurethanes. Inorganic support materials in powder form are preferred.

Supported catalysts of this type can generally contain 0.5 to 50% by weight, preferably 1 to 10% by weight, of the hydrogen-transferring substance, with respect to the total weight of the supported catalyst. The hydrogen-transferring substance can thus be distributed homogeneously in the support material, but catalysts are preferred in whose outer layer or on whose surface the hydrogen-transferring substance is deposited. The preparation and shaping of the catalysts, which can be used in process (e) can take place in a known manner (see, for example, Houben-Weyl, Methoden der organischen Chemie (Methods of Organic Chemistry), Volume IV, Ic, Part I, p. 16 to 26, Georg Thieme Verlag, Stuttgart, 1980).

Preferred supported catalysts are ruthenium on charcoal, ruthenium on aluminum oxide, rhodium on charcoal, rhodium on aluminum oxide, palladium on charcoal, palladium on aluminum oxide, palladium on calcium carbonate, palladium on barium sulphate, palladium on silica, platinum on charcoal and platinum on aluminum oxide, nickel on kieselguhr, nickel on alumin oxide and also nickel and palladium on aluminum oxide.

For hydrogenation in a heterogeneous system, preferred hydrogenation catalysts, which exclusively or preponderantly consist of a hydrogen-transferring substance, are, for example, oxidic catalysts, such as palladium oxide, platinum oxide, ruthenium oxide and/or rhodium oxide/platinum oxide according to Nishimura, and furthermore black catalysts preparable by reduction of corresponding metal salts or metal salt mixtures using alkali metal hydrides, alkali metal borohydrides, metal alkyls, hydrazine, formaldehyde, hydrogen or electropositive metals, such as palladium black, platinum black and rhodium black; and spongey catalysts of the Raney type, such as Raney nickel, Raney cobalt, Raney nickel/cobalt, Raney nickel/iron, Raney nickel/copper, Raney nickel/iron/chromium, Raney nickel/palladium and Raney nickel/iron/vanadium.

For hydrogenation in the heterogeneous system, the hydrogenation catalysts are employed in the second step of process (e) in such an amount that 0.5 to 2.5, preferably 0.1 to 1% by weight, of hydrogen-transferring substance is present with respect to the total weight of the reaction mixture.

When carrying out the second step of process (e) mixtures of two or more of the mentioned hydrogenation catalysts can also be used.

The catalytic activity of the hydrogenation catalysts generally remains to a large extent when carrying out the second step of process (e) so that this can be employed repeatedly with discontinuous procedures and can remain in use for a relatively long time with continuous procedures.

The reaction temperatures can be varied within a relatively wide range. In general, the reaction is carried out in the range between 0° C. and 150° C., preferably between 20° C. and 120° C.

The heterogeneously catalyzed hydrogenations in the second step of process (e) are preferably carried out at elevated pressure. In general, the reaction is carried out between 1 and 150 bar, preferably between 10 and 60 bar.

In addition to the mentioned hydrogenation catalysts of the heterogeneous type, hydrogenation catalysts, dissolved to form a homogeneous solution can also be used for carrying out the second step of process (e). The often higher selectivity of homogeneous hydrogenation catalysts in comparison to heterogeneous catalysts permits the selective hydrogenation of cyclopropyl ketones of the formulae (V-a) or (V-b), which additionally contain hydrogenatable or hydrogenolysis-sensitive substituents, such as, for example, halogen on the phenyl radical. Such homogeneous hydrogenation catalysts are, for example, complexes which contain metals of the eighth subgroup of the periodic table of the elements according to Mendeleev as the central atom. Preferred metals here are ruthenium, rhodium, palladium, iridium, cobalt and nickel. Ruthenium, rhodium and iridium are particularly preferred. Examples of metal complexes of this type which may be mentioned are tris-(triphenylphosphine)-rhodium(I) chloride, tris-(triphenylphosphine)-ruthenium(II) chloride and bis-(triphenylphosphine)-carbonyl-iridium(I) chloride.

Suitable diluents in the case of the use of hydrogenation catalysts, dissolved to form a homogeneous solution, when carrying out the second step of process (e) are inert organic solvents. Alcohols, such as methanol, ethanol, isopropanol or ethylene glycol, and furthermore hydrocarbons, such as toluene, and in addition ketones, such as acetone and butanone, and also esters, such as ethyl acetate are preferably utilizable.

For hydrogenation in the homogeneous system, the hydrogenation catalysts are generally employed for carrying out the second step of process (e) in such an amount that 0.01 to 2.5 mole-%, preferably 0.05 to 1.0 mole-%, of hydrogenation catalyst complex is present with respect to the cyclopropyl ketone of the formula (V-a) or (V-b) employed.

The reaction temperatures can also be varied within a relatively wide range for hydrogenation in the homogeneous system when carrying out the second step of process (e). In general, the reaction is carried out at temperatures between 0° C. and 150° C., preferably between 20° C. and 120° C.

The hydrogenations carried out in the homogeneous system in the second step of process (e) are preferably performed at elevated pressure. In general, the reaction is carried out at pressures between 1 and 150 bar, preferably between 10 and 100 bar.

In a variant, the hydrogenation in the homogeneous system in the second step of process (e) can also be carried out so that molecular hydrogen is not used for hydrogenation but reducing agents are employed which are capable, in the presence of a suitable catalyst, of transfering one or more hydrogen atoms to the cyclopropyl ketone of the formula (V-a) or (V-b) in the sense of a transfer hydrogenation and therefore acting as hydrogen donors. Suitable catalysts for such a transfer hydrogenation are, in principle, the complexes of metals of the eighth subgroup of the periodic table of the elements according to Mendeleev which have already been described for the homogeneously catalyzed hydrogenation using molecular hydrogen in the second step of process (e).

Possible hydrogen donors here are primary and secondary monohydric or polyhydric alcohols. Methanol, ethanol, n-propanol, i-propanol, n-butanol, 2-butanol, benzyl alcohol, ethylene glycol, 1,3-propane-diol, 1,4-butanediol and 1,5-pentanediol are preferably utilizable. These alcohols can serve both as hydrogen donors and also as solvents.

Further hydrogen donors which can be employed in the second step of process (e) are alkali metal salts and alkaline earth metal salts of formic acid, such as sodium formate and potassium formate, and also formic acid itself. In the use of a salt of formic acid, the second step of process (e) can be carried out in the form of a phase-transfer catalysis, by means of which the cyclopropyl ketone of the formula (V-a) or (V-b) and the hydrogenation catalyst are dissolved in a suitable inert solvent and the formate is present in a second phase as an aqueous solution. In this connection, suitable solvents are therefore those solvents which on the one hand dissolve the cyclopropyl ketone of the formula (V-a) or (V-b) and the hydrogenation catalyst, but on the other hand are immiscible with water. Solvents of this type are, for example, benzene, toluene, chlorobenzene, dichlorobenzenes and methylene chloride. Possible phasetransfer catalysts are all reaction accelerators employable in organic chemistry for this purpose. Tetrabutylammonium bromide and methyl-tridecyl-ammonium chloride (Aliquat ® 336) are preferably utilizable.

The reaction time necessary for the second step of process (e) is dependent on the reaction temperature, the hydrogen partial pressure, the intensity of mixing of the reaction mixture and the activity and concentration of the hydrogenation catalyst. In general, the necessary reaction time is in the range from 15 minutes up to several hours. Working up takes place by customary methods in each case.

The acetylenes of the formula (XI) required as starting materials for carrying out process (f) are known or can be prepared in a simple manner by processes which are known in principle.

The acid halides of the formula (XII) required as reaction components for carrying out process (f) are also known or can be prepared by processes which are known in principle.

Suitable catalysts for carrying out process (f) are all reaction accelerators customary for reactions of this type. Copper salts, such as, for example, copper iodide are preferably utilizable.

Possible diluents for carrying out process (f) are all inert organic solvents customary for reactions of this type. Ethers, such as tetrahydrofuran and diethyl ether are preferably utilizable.

The reaction temperatures can be varied within a certain range when carrying out process (f). In general, the reaction is carried out at temperatures between −78° C. and +50° C., preferably between −78° C. and +40° C.

When carrying out process (f), 1 to 1.2 moles of acid halide of the formula (XII) and also catalyst are generally employed per mole of acetylene of the formula (XI). Working up takes place of customary methods.

The dimethyl-oxo-sulphonium methylide of the formula (VI) required as reaction component in process (c) is known (compare J. Am. Chem. Soc. 87, 1363–1364 (1965)). It is used in the above reaction in the freshly prepared state by preparing it in situ by reaction of trimethyloxosulphonium iodide with sodium hydride or sodium amide, in particular with potassium tert.-butylate or sodium methylate, in the presence of a diluent.

The dimethylsulphonium methylide of the formula (VII) additionally possible as reaction component in process (c) is also known (compare Heterocycles 8, 397 (1977)). It is also used in the above reaction in the freshly prepared state, by preparing it in situ, for example, from trimethylsulphonium halide or trimethylsulphoniummethylsulphate, in the presence of a strong base, such as, for example, sodium hydride, sodium amide, sodium methylate, potassium tert.-butylate or potassium hydroxide, in the presence of a diluent, such as tert.-butanol or dimethyl sulphoxide.

Suitable diluents for carrying out process (c) are inert organic solvents. Alcohols, such as tert.-butanol, ethers, such as tetrahydrofuran or dioxane, and furthermore aliphatic and aromatic hydrocarbons, such as benzene, toluene or xylene, and also strongly polar solvents, such as dimethylsulphoxide are preferably utilizable.

The reaction temperatures can be varied within a relatively wide range when carrying out process (c). In general, the reaction is carried out between 0° C. and 100° C., preferably between 10° C. and 60° C.

When carrying out process (c), 1 to 3 moles of dimethyloxosulphonium methylide of the formula (VI) or dimethylsulphonium methylide of the formula (VII) are generally employed per mole of cyclopropyl ketone of the formula (V). The isolation of the oxiranes of the formula (II) takes place by customary methods.

The carbinols of the formula (VIII) required as starting materials for carrying out process (d) were hitherto unknown. They can be prepared by reacting (g) halogenoketones of the formula

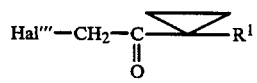
$$\text{Hal}'''-CH_2-\underset{\underset{O}{\|}}{C}-R^1 \qquad (XIII)$$

in which $R^1$ has the abovementioned meaning and
Hal''' represents chlorine or bromine, with acetylene salts of the formula

$$R^2-C\equiv C\ Me \qquad (XIV)$$

in which
$R^2$ has the abovementioned meaning and
Me represents an equivalent of a metal cation,
if appropriate in the presence of an acid-binding agent and in the presence of a diluent.

Some of the halogenoketones of the formula (XIII) required as starting materials for process (g) are known (Belgian Patent Specification 879,785 and DE-OS (German Published Specification) 2,944,342). They can be prepared by reacting (h) methyl-cyclopropyl ketones of the formula

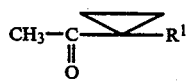

(X)

in which
R¹ has the abovementioned meaning,
with chlorinating agents or brominating agents in the presence of a diluent.

Possible chlorinating agents and brominating agents for process (h) are all chlorinating and brominating reagents customary for reactions of this type. Sulphuryl chloride, sulphuryl bromide and bromine are preferably utilizable.

Suitable diluents for process (h) are all inert organic solvents customary for reactions of this type. Halogenated aliphatic hydrocarbons, such as methylene chloride, chloroform and carbon tetrachloride are preferably utilizable.

The reaction temperatures can be varied within a certain range in process (h). In general, the reaction is carried out at temperatures between $-10°$ C. and $+60°$ C., preferably between $0°$ C. and $+40°$ C.

When carrying out process (h), the reaction is carried out at atmospheric pressure. However, it is also possible to work at elevated or reduced pressure in each case.

When carrying out process (h), a stoichiometric amount or even a slight excess of chlorinating or brominating agent is generally employed per mole of ketone of the formula (X). Working up takes place by customary methods. In general, a procedure is used in which the reaction mixture is washed successively with dilute aqueous sodium hydrogen carbonate solution and water, then dried and concentrated.

Formula (XIV) provides a general definition of the acetylene salts required as reaction components in process (g). In this formula, R² preferably has those meanings which have already been mentioned as preferable for this radical in connection with the description of the substances of the formula (I) according to the invention. Me preferably represents a lithium cation or an equivalent of a cerium (III) cation.

The acetylene salts of the formula (XIV) are known or can be prepared by processes which are known in principle.

Suitable acid-binding agents for carrying out process (g) are all customary acid acceptors.

Possible diluents for carrying out process (g) are all customary inert organic solvents. Aromatic hydrocarbons, such as toluene, and additionally ethers, such as diethyl ether, tetrahydrofuran, tert.-butylmethyl ether and mixtures of these ethers are preferably utilizable.

The reaction temperatures can be varied within a relatively wide range when carrying out process (g). In general, the reaction is carried out at temperatures between $-100°$ C. and $+100°$ C., preferably between $-80°$ C. and $+50°$ C.

Process (g) is generally carried out at atmospheric pressure. However, it is also possible to work at elevated or reduced pressure.

When carrying out process (g), 1 to 3 moles of acetylene salt of the formula (XIV) are generally employed per mole of halogenoketone of the formula (XIII). Working up takes place by customary methods.

Possible bases for carrying out process (d) are all organic and inorganic acid-binding agents customarily suitable for reactions of this type. Alkali metal carbonates, such as sodium carbonate and potassium carbonate, and furthermore alkali metal hydroxides, such as sodium hydroxide and potassium hydroxide, and additionally alkali metal alcoholates, such as sodium methylate and potassium methylate, and sodium ethylate and potassium ethylate, and also potassium tert.-butylate, and furthermore lower tertiary alkylamines, cycloalkylamines and aralkylamines, such as triethylamine in particular are preferably utilizable.

Possible diluents for carrying out process (d) are all customary inert organic solvents. Nitriles, such as acetonitrile, and furthermore aromatic hydrocarbons, such as benzene, toluene and dichlorobenzene, and additionally formamides, such as dimethylformamide, and also strongly polar solvents, such as dimethyl sulphoxide and hexamethylphosphoric triamide are preferably utilizable.

The reaction temperatures can be varied within a certain range when carrying out process (d). In general, the reaction is carried out at temperatures between $-20°$ C. and $+100°$ C., preferably between $0°$ C. and $60°$ C.

When carrying out process (d), the reaction is generally carried out at atmospheric pressure. However, it is also possible to work at elevated or reduced pressure.

When carrying out process (d), 1 to 3 moles of base are generally employed per mole of carbinol of the formula (VIII). Working up takes place by customary methods.

The azoles of the formula (III) required as reaction components for carrying out process (a) according to the invention are generally known compounds of organic chemistry.

Suitable acid-binding agents for carrying out process (a) according to the invention are all customary acid acceptors. Alkali metal carbonates and hydrogen carbonates, such as sodium carbonate, potassium carbonate or sodium hydrogen carbonate and, furthermore, hydroxides and alcoholates of alkali metals, such as sodium hydroxide, potassium hydroxide, sodium methylate or potassium tert.-butylate, and additionally tertiary aliphatic or aromatic amines, such as triethylamine, N,N-dimethylcyclohexyl-amine, N,N-dimethyl-benzylamine, and pyridine, and in addition cyclic amines, such as 1,5-diaza-bicyclo-[4,3,0]-non-5-ene (DBN), 1,8-diaza-bicyclo[5,4,0]undec-7-ene (DBU) and 1,4-diazabicyclo[2,2,2]octane (DABCO) are preferably utilizable.

Possible diluents for carrying out process (a) according to the invention are all customary inert organic solvents. Nitriles, such as acetonitrile in particular; aromatic hydrocarbons, such as benzene, toluene and dichlorobenzene; formamides, such as dimethylformamide in particular, and also hexamethylphosphoric triamide are preferably utilizable.

The reaction temperatures can be varied within a relatively wide range when carrying out process (a) according to the invention. In general, the reaction is carried out at temperatures between $0°$ C. and $200°$ C., preferably between $50°$ and $150°$ C.

When carrying out process (a) according to the invention, 1 to 4 moles or azole of the formula (III) and 1 to 2 moles of base are preferably employed per mole of oxirane of the formula (II). The isolation of the final products takes place in a customary manner.

The hydroxyalkylazolyl derivatives of the formula (Ia) required as starting materials for process (b) according to the invention are compounds according to the invention. Their conversion into the corresponding alcoholates takes place in a generally known manner, by reacting them with suitable strong bases, such as amides or hydrides of alkali metals, quaternary amonium hydroxides or phosphonium hydroxides in an inert diluent, such as, for example, dioxane, at room temperature. Accordingly, $R^9$ in the compounds of the formula (Ib) preferably represents an alkali metal cation, such as a sodium or potassium cation, or a quaternary ammonium or phosphonium cation.

Formula (IV) provides a general definition of the halogen compounds additionally required as starting materials for process (b) according to the invention. In this formula, $R^{10}$ preferably represents the meanings which have already been mentioned for the substituent $R^1$ in connection with the description of the substances of the formula (I) according to the invention, with the exception of the meaning of hydrogen. Hal preferably represents chlorine or bromine.

The halogen compounds of the formula (IV) are known or can be prepared by methods which are known in principle.

Suitable diluents for carrying out process (b) according to the invention are inert organic solvents. These preferably include ethers, such as diethyl ether or dioxane, aromatic hydrocarbons, such as benzene, and in individual cases also chlorinated hydrocarbons, such as chloroform, methylene chloride or carbon tetrachloride, and also hexamethylphosphoric triamide.

The reaction temperatures can be varied within a relatively wide range when carrying out process (b) according to the invention. In general, the reaction is carried out between 0° C. and 120° C., preferably between 20° C. and 100° C.

When carrying out process (b) according to the invention, hydroxy compounds of the formula (Ia) are initially converted to the corresponding alcoholates of the formula (Ib) using strong bases. In the step which then follows, 1 to 2 moles of halogen compound of the formula (IV) are preferably employed per mole of an alcoholate of the formula (Ib).

For the isolation of the final products, the reaction mixture is freed from solvent, and water and an organic solvent are added to the residue. The organic phase is separated off, worked up in a customary manner and purified.

In a preferred embodiment, a procedure is advantageously used in which, starting from a hydroxy compound of the formula (Ia), the latter is converted by means of alkali metal hydride or alkali metal amide in a suitable organic solvent into the alkali metal alcoholate and the latter is immediately reacted without isolation with a halogen compound of the formula (IV), by means of which the compounds of the formula (I) according to the invention are obtained in one operation with the elimination of alkali metal halide.

According to a further preferred embodiment, the preparation of the alcoholates and also the reaction with a halogen compound of the formula (IV) is advantageously carried out in a two phase system, such as, for example, aqueous sodium hydroxide solution or potassium hydroxide solution/toluene or methylene chloride, with the addition of 0.01–1 mole of a phase-transfer catalyst, such as, for example, ammonium or phosphonium compounds, by means of which the alcoholates are reacted in the organic phase or on the boundary surface with the halides present in the organic base.

The hydroxyalkyl-azolyl derivatives of the formula (I) obtainable by the processes according to the invention can be converted into acid addition salts or metal salt complexes.

For the preparation of acid addition salts of the compounds of the formula (I), suitable acids are preferably those which have already been mentioned as preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtering off, and can be purified, if necessary by washing with an inert organic solvent.

For the preparation of metal salt complexes of the compounds of the formula (I), suitable salts of metals are preferably those which have already been mentioned as preferred metal salts in connection with the description of the metal salt complexes according to the invention.

The metal salt complexes of the compounds of the formula (I) can be obtained in a simple manner by customary processes, thus, for example, by dissolving the metal salt in alcohol, for example ethanol and adding to compounds of the formula (I). The metal salt complexes can be isolated in a known manner, for example by filtering off, and can be purified, if necessary, by recrystallization.

The active compounds according to the invention exhibit a strong microbicidal action and can be employed as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae;* Pseudomonas species, such as *Pseudomonas lachrymans;* Erwinia species, such as *Erwinia amylovora;* Pythium species, such as *Pythium ultimum;* Phytophthora species, such as *Phytophthora infestans;* Pseudoperonospora species, such as *Pseudoperonospora humuli* or *Pseudoperonospora cubense;* Plasmopara species, such as *Plasmopara viticola;* Peronospora species, such as *Peronospora pisi* or *P. brassicae;* Erysiphe species, such as *Eyrsiphe graminis;* Sphaerotheca species, such as *Sphaerotheca fuliginea;* Podosphaera species, such as *Podosphaera leucotricha;* Venturia species, such as Venturia inaequalis; Pyrenophora species, such as Pyrenophora teres or *P. graminea;* (conidia form: Drechslera, syn: Helminthosporium); Cochliobolus species, such as *Cochliobolus sativus;* (conidia form: Drechslera, syn: Helminthosporium); Uromyces species, such as *Uromyces appendiculatus;* Puccinia species, such as *Puccinia recondita;* Tilletia species, such as *Tilletia caries;* Ustilago species, such as *Ustilago nuda* or *Ustilago avenae;* Pellicularia species, such as *Pellicularia sasakii;* Pyricularia species, such as *Pyricularia oryzae;* Fusarium species, such as *Fusarium culmorum;* Botrytis species, such as *Botrytis cinerea;* Septoria species, such as *Septoria nodorum;* Leptosphaeria species, such as *Leptosphaeria nodorum;* Cercospora species, such as *Cercospora canescens;* Alternaria species, such as *Alternaria brassicae* and Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are especially suitable for combating diseases in cereals and rice. Mildew and rust, *Puccinia recondita, Leptosphaeria nodorum, Pyrenophora teres, Cochliobolus sativus* and *Pseudocercosporella herpotrichoides* in cereals, and Pyricularia and Pellicularia in rice can thus be combated particularly well. The compounds additionally possess a very good in-vitro action.

In addition, the active compounds according to the invention also possess plant growth-regulating properties.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating substances can be employed, for example, to inhibit vegetative growth of the plants. Such inhibition of growth is, inter alia, of economic interest in the case of grasses, since it is thereby possible to reduce the frequency of cutting the grass in ornamental gardens, parks and sports grounds, on road verges, at airports or in fruit orchards. The inhibition of growth of herbaceous and woody plants on road verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beets, sugar cane, pineapples and citrus fruit or to increase the protein content in soy beans or cereals. Using growth regulators it is also possible, for example, to inhibit the degradation of desired constituents, such as, for example, sugar in sugar beets or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can in some cases improve the coloration of fruit. In addition, concentrating the ripening within a certain period of time is also achievable with the aid of growth regulators. This provides the preconditions for being able to carry out complete mechanical or manual harvesting in a single pass, for example in the case of tobacco tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Repeating the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The compounds according to the invention can be preferably used for inhibiting the growth of cereals and grass.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well a their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under atmospheric pressure, for example aerosol propellants, such as halogenated hydrocarbons as well as butane, propane, nitrogen and carbon dioxide; as solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products; as dispersing agents there are suitable: for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in a customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the substances according to the invention are used as fungicides, the amounts applied can be varied within a relatively wide range depending on the type of application. The active compound concentrations in the use forms for the treatment of plant parts are thus generally between 1 and 0.0001% by weight, preferably between 0.5 and 0.001%. For seed treatment, active compound amounts of 0.001 to 50 g per kilogram of seed, preferbly 0.01 to 10 g, are generally required. For treatment of the soil, active compound concentrations of 0.00001 to 0.1% by weight, preferably 0.0001 to 0.02%, are necessary at the site of action.

When the compounds according to the invention are used as plant growth regulators, the amounts applied can be varied within a relatively wide range. In general, 0.01 to 50 kg, preferably 0.05 to 10 kg, of active compound are used per hectare of soil surface.

When the substances according to the invention are used as plant growth regulators, they are to be used within a preferred period of time, the exact definition of which depends on the climatic and vegetative circumstances.

The preparation and the use of the active compounds according to the invention can be seen from the following examples taken in conjunction with the accompanying drawings wherein FIGS. 1 to 18 are NMR spectra of various novel compounds as set forth in Table 3 hereinbelow:

PREPARATION EXAMPLES

EXAMPLE 1

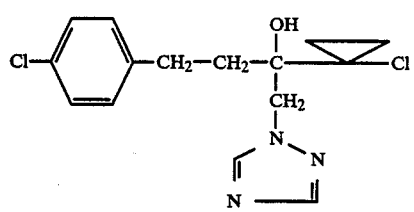 (I-1)

A solution of 13.4 g (0.05 mol) of 2-(1-chlorocyclopropyl)-2-(4-chlorophenylethyl)-oxirane in 20 ml of acetonitrile are added dropwise under a nitrogen atmosphere to a mixture of 10 g of potassium carbonate, 15 g (0.22 mol) of 1,2,4-triazole and 50 ml of acetonitrile, and the reaction mixture is heated under reflux. After completion of the addition, the reaction mixture is stirred for a further 8 hours under reflux, the residue is filtered off with suction and the filtrate is concentrated by stripping off the solvent under reduced pressure. The residue remaining is taken up in ethyl acetate, and the organic phase is washed using water, dried over sodium sulphate and concentrated by stripping off the solvent under reduced pressure. The resulting residue is chromatographed on a silica gel column using chloroform/ethanol=98:2 as eluant. After recrystallization of the product thus remaining from cyclohexane, 5.1 g (30% of theory) of 2-(1-chlorocyclopropyl)-4-(4-chlorophenyl)-1-(1,2,4-triazol-1-yl)-butan-2-ol are obtained in the form of a solid substance of melting point 137° C.

Preparation of starting substances:

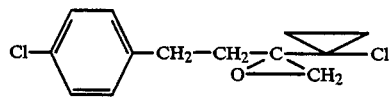 (II-1)

16 ml (0.22 mol) of dimethyl sulphide and 24.2 g (0.19 mol) of dimethyl sulphate are added to 30 ml of tert.-butanol and the mixture is allowed to stand for 14 hours at 20° C. A solution of 17 g (0.07 mol) of 1-chlorocyclopropyl 4-chlorophenylethyl ketone in 70 ml of tert.-butanol is initially added dropwise with stirring to the reaction mixture and 22 g of potassium hydroxide powder are then introduced, the temperature of the reaction mixture being held t 20° to 30° C. The mixture is stirred for a further 3 hours at 30° C., then the dimethyl sulphide is stripped off under reduced pressure and the reaction mixture is then poured into 50 ml of a 1% strength aqueous hydrogen peroxide solution. The mixture is extracted using ethyl acetate. The organic phase is washed using water and is concentrated by stripping off the solvent under reduced pressure after drying over sodium sulphate. In this manner, 13.4 g (75% of theory) of 2-(1-chlorocyclopropyl)-2-(4-chlorophenylethyl)-oxirane are obtained in the form of an oily product, which is further reacted without additional purification.

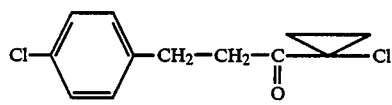 (V-1)

460 mg (0.5 mmol) of tris-triphenylphosphinerhodium chloride (=1 mol %, with respect to the reaction component) are added to a 100 ml autoclave. After purging with nitrogen, an air-free solution of 12 g (0.05 mol) of 1-chlorocyclopropyl 4-chlorophenyl-ethenyl ketone in 40 ml of toluene is added and the mixture is heated to 50° C. under a hydrogen pressure of 30 bar. The hydrogen pressure is held between 40 and 50 bar until gas uptake has ended (after about 1 hour). The mixture is then allowed to react for a further hour. For working up, the solvent is stripped off under reduced pressure and the remaining residue is purified on silica gel using dichloromethane as eluant. 11 g (90% of theory) of 1-chlorocyclopropyl 4-chlorophenylethyl ketone are obtained in the form of an oily product.

$^1$H-NMR (200 MHz, CDCl$_3$);

$\delta$=1.28–1.38 (m, 2H), 1.57–1.67 (m, 2H), 2.84 (t, 2H), 3.15 (t, 2H), 7.08–7.29 (m, 4H).

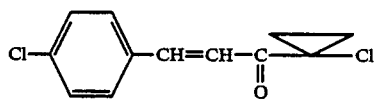 (V-2)

50 ml of water and 10 pellets of solid sodium hydroxide are added at room temperature to a mixture of 60 g (0.5 mol) of 1-chlorocyclopropylmethyl ketone, 70 g (0.5 mol) of 4-chlorobenzaldehyde and 250 ml of ethanol. The mixture is stirred at room temperature for 16 hours. The precipitated solid is then filtered off with suction. In this manner, 108.5 g (89% of theory) of 1-chlorocyclopropyl 4-chlorophenyl-ethenyl ketone are obtained in the form of a solid substance of melting point 92° C.

EXAMPLE 2

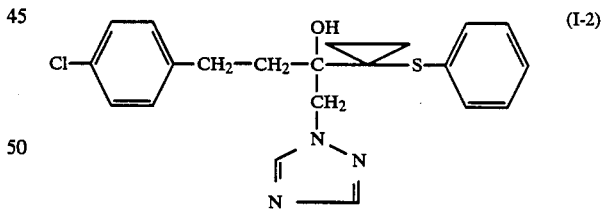 (I-2)

A solution of 25.6 g (0.1 mol) of 2-(4-chlorophenylethyl)-2-(1-phenylmercapto-cyclopropyl)-oxirane in 30 ml of acetonitrile is added dropwise under a nitrogen atmosphere to a mixture of 14 g of potassium carbonate, 21 g (0.3 mol) of 1,2,4-triazole and 70 ml of acetonitrile, and the reaction mixture is heated under reflux. After completion of the addition, the mixture is stirred for a further 8 hours under reflux, the residue is filtered off with suction and the filtrate is concentrated by stripping off the solvent under reduced pressure. The residue remaining is taken up in ethyl acetate/toluene, and the organic phase is washed using water, dried over sodium sulphate and concentrated by stripping off the solvent under reduced pressure. The resulting precipitate is chromatographed on a silica gel column using chloroform/ethanol=99:1 as eluant. After recrystallization of the remaining residue from cyclohexane, 11.1 g (37% of theory) of 4-(4-chlorophenyl)-2-(1-phenylmercaptocyclopropyl)-1-(1,2,4-triazol-1-yl)-butan-2-ol are obtained in the form of a solid of melting point 137° C.

Preparation of starting substances:

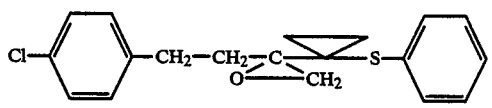 (II-2)

21 ml (0.29 mol) of dimethyl sulphide and 32.5 g (0.26 mol) of dimethyl sulphate are added to 40 ml of tert.-butanol and the mixture is allowed to stand at room temperature for 14 hours. A solution of 30 g (0.095 mol) of 4-chlorophenylethyl 1-phenylmercapto-cyclopropyl ketone in 90 ml of tert.-butanol is initially added dropwise to the reaction mixture with stirring and 29.2 g of potassium hydroxide powder are then introduced, the temperature of the reaction mixture being held at 20° to 30° C. The mixture is stirred for a further 3 hours at 30° C., then the dimethyl sulphide is stripped off under reduced pressure and the reaction mixture is then poured into 70 ml of a 1% strength aqueous hydrogen peroxide solution. The mixture is extracted with ethyl acetate. The organic phase is washed using water and concentrated by stripping off the solvent under reduced pressure after drying over sodium sulphate. In this manner, 25.6 g (82% of theory) of 2-(4-chlorophenylethyl)-2-(1-phenylmercapto-cyclopropyl)-oxirane are obtained in the form of an oily product, which is further reacted without additional purification.

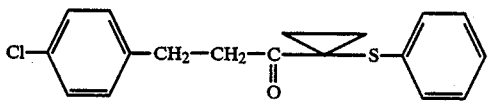 (V-3)

460 mg (0.5 mmol) of tris-triphenylphosphinerhodium chloride (=1 mol-%, with respect to the reaction component) are added to a 100 ml autoclave. After purging with nitrogen, an air-free solution of 15.7 g (0.05 mol) of 4-chlorophenyl-ethenyl 1-phenylmercapto-cyclopropyl ketone in 40 ml of toluene is added and the mixture is heated at 50° C. under a hydrogen pressure of 30 bar. The hydrogen pressure is held between 40 and 50 bar until gas uptake has ended. The mixture is then reacted for a further hour. For working up, the solvent is stripped off under reduced pressure and the residue remaining is purified on silica gel using dichloromethane as eluant. 14.2 g (90% of theory) of 4-chlorophenylethyl 1-phenylmercaptocyclopropyl ketone are obtaned in the form of an oily product.

¹H-NMR (200 MHz, CDCl₃);
δ=1.25–1.35 (m, 2H), 1.75–1.90 (m, 2H), 2.79 (t, 2H), 3.18 (t, 2H), 6.95–7.45 (m, 9H).

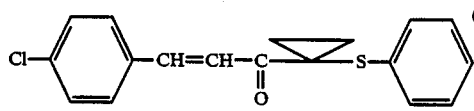 (V-4)

50 ml of water and 8 pellets of solid sodium hydroxide are added at room temperature to a mixture of 75 g (0.39 mol) of 1-phenylmercaptocyclopropyl methyl ketone, 56 g (0.39 mol) of 4-chlorobenzaldehyde and 200 ml of ethanol. The mixture is stirred at room temperature for 14 hours. The precipitated solid is then filtered off with suction. In this manner, 120.3 g (98% of theory) of 4-chlorophenyl-ethenyl 1-phenylmercaptocyclopropyl ketone are obtained in the form of a solid substance.

¹H-NMR (200 MHz, CDCl₃);
δ=1.32–1.41 (m, 2H), 1.87–1.95 (m, 2H), 7.05–7.84 (m, 11H).

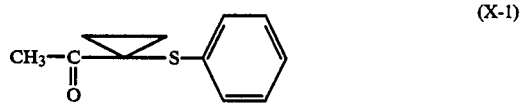 (X-1)

A solution of 134 g (0.83 mol) of bromine in 130 ml of methylene chloride is added dropwise at 10° C. with stirring to a solution of 100 g (0.83 mol) of 5-chloropentan-2-one in 400 ml of methylene chloride. The reaction mixture is stirred for a further hour at room temperature, then washed using water and dilute aqueous sodium carbonate solution and dried over sodium sulphate. The mixture is concentrated by stripping off the solvent under reduced pressure, the residue is taken up in 200 ml of methanol and 91.5 g (0.83 mol) of thiophenol are added at 5° C. with stirring. A mixture of 93 g of potassium hydroxide powder in 500 ml of methanol is then added dropwise. The reaction mixture is initially stirred for 2 hours at room temperature and then for 4 hours at 40° C. The mixture is then concentrated by stripping off the solvent under reduced pressure and the remaining residue is taken up in methylene chloride. The organic solution is washed successively using water, dilute aqueous sodium hydroxide solution and again using water, then concentrated under reduced pressure and then subjected to a vacuum distillation. In this manner, 76.8 g (48% of theory) of methyl 1-phenyl-mercaptocyclopropyl ketone of boiling point 155° C./20 mbar are obtained.

EXAMPLE 3 AND 4

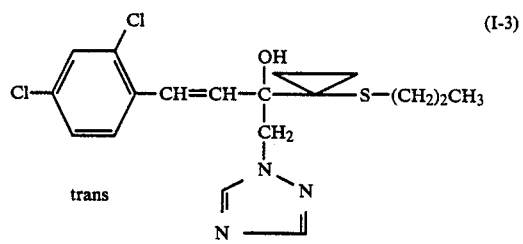 (I-3)

A solution of 38.2 g (0.12 mol) of 2-(2,4-dichlorophenyl-ethenyl)-2-(1-propylmercaptocyclopropyl)-oxirane in 30 ml of dimethylformamide is added dropwise at 80° C. under a nitrogen atomsphere and with stirring to a mixture of 24 g (0.35 mol) of 1,2,4-triazole, 2.7 g (0.02 mol) of potassium tert.-butylate and 50 ml of dimethylformamide. The mixture is stirred for 6 hours at 80° C., then the solvent is stripped off under reduced pressure, and the residue is taken up in ethyl actate/toluene, washed using water, dried over sodium sulphate and concentrated under reduced pressure. The residue remaining is chromatographed on silica gel using chloroform as eluant. In this manner, 12.1 g (26% of theory) of trans-4-(2,4-dichlorophenyl)-2-(1-propylmercaptocyclopropyl)-1-(1,2,4-triazol-1-yl)-but-3-en-2-ol are obtained in the form of an oily product.

¹H-NMR (200 MHz, CDCl₃):

δ=0.75-1.65 (m, 9H), 2.63 (t, 2H), 4.62 (d, 1H), 4.73 (d, 1H), 6.30 (d, 1H), 6.90 (d, 1H), 7.12-7.42 (m, 3H), 7.90 (s, 1H), 8.17 (s, 1H).

1.8 g (4% of theory) of cis-4-(2,4-dichlorophenyl)-2-(1-propylmercaptocyclopropyl)-1-(1,2,4-triazol-1-yl)-but-3-en-2-ol are additionally isolated (Compound I-4).

¹H-NMR (200 MHz, CDCl₃):

δ=0.75-1.10 (m, 7H), 1.50 (sex, 2H), 2.40 (t, 2H), 4.35-4.53 (m, 3H), 5.97 (d, 1H), 7.00 (d, 1H), 7.20-7.44 (m, 3H), 7.92 (s, 1H), 8.13 (s, 1H).

Preparation of starting substances:

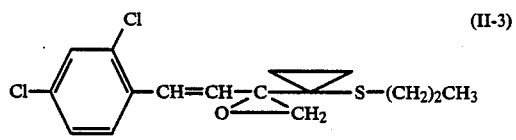

30 ml (0.41 mol) of dimethyl sulphide and 43.5 g (0.35 mol) of dimethyl sulphate are added to 60 ml of tert.-butanol and allowed to stand at room temperature for 14 hours. A solution of 40 g (0.13 mol) of 2,4-dichlorophenyl-ethenyl 1-propylmercaptocyclopropyl ketone in 120 ml of tert.-butanol is initially added dropwise to the reaction mixture with stirring and then 39.1 g of potassium hydroxide powder is introduced, the temperature of the reaction mixture being held at 20° to 30° C. The mixture is stirred for a further 3 hours at 30° C., then the dimethyl sulphide is stripped off under reduced pressure and the reaction mixture is then poured into 70 ml of a 1% strength aqueous hydrogen peroxide solution. The mixture is extracted with ethyl acetate. The organic phase is washed using water and concentrated by stripping off the solvent under reduced pressure after drying over sodium sulphate. In this manner, 38.2 g (91% of theory) of 2-(2,4-dichlorophenylethenyl)-2-(1-propylmercaptocyclopropyl)-oxirane are obtained in the form of an oily product, which is further reacted without additional purification.

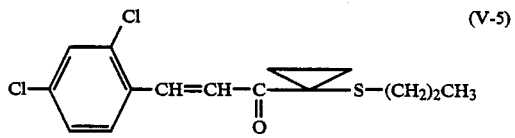

5 pellets of solid sodium hydroxide are added at room temperature to a mixture of 41.7 g (0.26 mol) of 1-acetyl-1-propylmercapto-cyclopropane, 46 g (0.26 mol) of 2,4-dichlorobenzaldehyde, 130 ml of ethanol and 30 ml of dichloromethane. The mixture is stirred for a further 14 hours at room temperature. 50 ml of water are added, and the oil phase is separated off and taken up in dichloromethane. The organic phase is washed using water, dried over sodium sulphate and concentrated by stripping off the solvent under reduced pressure. In this manner, 80 g (97% of theory) of 2,4-dichlorophenylethenyl 1-propylmercaptocyclopropyl ketone (cis-trans isomers) are obtained in the form of an oily product.

¹H-NMR (200 MHz, CDCl₃);

δ=0.95 (t, 3H), 1.19-1.29 (m, 2H), 1.50-1.70 (m, 4H), 2.57 (t, 2H), 7.20-7.95 (m, 5H).

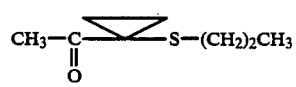

A solution of 134 g (0.83 mol) of bromine in 130 ml of methylene chloride is added dropwise at 10° C. with stirring to a solution of 100 g (0.83 mol) of 5-chloropentan-2-one in 400 ml of methylene chloride. The reaction mixture is stirred for a further hour at room temperature, then washed using water and dilute aqueous sodium carbonate solution and dried over sodium sulphate. The mixture is concentrated by stripping off the solvent under reduced pressure, and the residue is taken up in 200 ml of methanol and 63 g (0.83 mol) of n-propylmercaptan are added at 5° C. with stirring. A mixture of 93 g of potassium hydroxide powder in b 500 ml of methanol is then added dropwise. The reaction mixture is initially stirred for 2 hours at room temperature and then for 4 hours at 40° C. The mixture is then concentrated by stripping off the solvent under reduced pressure and the remaining residue is taken up in methylene chloride. The organic solution is washed successively using water, dilute aqueous sodium hydroxide solution and again using water, then concentrated under reduced pressure and then subjected to a vacuum distillation. In this manner, 42 g (32% of theory) of 1-acetyl-1-propylmercaptocyclopropane of boiling point 107° C./20 mbar are obtained.

EXAMPLE 5

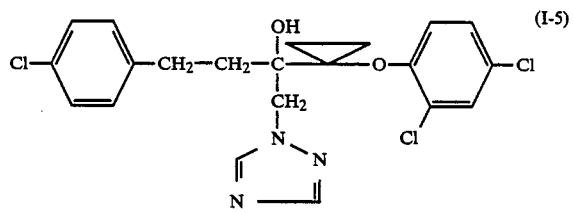

4-(4-Chlorophenyl)-2-[1-(2,4-dichlorophenoxy)cyclopropyl]-1-(1,2,4-triazol-1-yl)-butan-2-ol is also obtained in the form of an oily product by the previously given methods.

¹H-NMR (200 MHz, CDCl₃);

δ=0.25 | 0.45 (m, 2H), 0.67-0.83 (m, 1H), 0.83-1.05 (m, 1H), 1.80-2.15 (m, 2H), 2.70-2.90 (m, 1H), 2.90-3.13 (m, 1H), 4.16 (s, 1H), 4.38 (d, 1H), 4.70 (d, 1H), 7.00-7.40 (m, 7H), 8.02 (s, 1H), 8.38 (s, 1H).

The substances shown in the following Table 3 were also obtained according to the methods which were described in the previously given examples.

TABLE 3

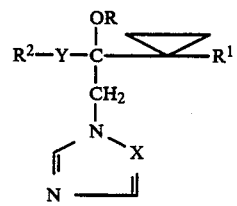
(I)

| Compound No. | R² | Y | R¹ | R | X | Characterization by |
|---|---|---|---|---|---|---|
| I-6 | 4-Cl-phenyl | —CH₂—CH₂— | —SCH₃ | H | N | m.p. = 115° C. |
| I-7 | 2,4-diCl-phenyl | —CH₂—CH₂— | —S(CH₂)₂CH₃ | H | N | NMR spectrum FIG. 1 |
| I-8 | 4-Cl-phenyl | —CH₂—CH₂— | —SCH(CH₃)₂ | H | N | NMR spectrum FIG. 2 |
| I-9 | 2,4-diCl-phenyl | —CH₂—CH₂— | —SC₂H₅ | H | N | NMR spectrum FIG. 3 |
| I-10 | 4-Cl-phenyl | —CH₂—CH₂— | —S—CH₂—phenyl | H | N | NMR spectrum FIG. 4 |
| I-11 | 2,4-diF-phenyl | —CH₂—CH₂— | Cl | H | N | NMR spectrum FIG. 5 |
| I-12 | 4-F-phenyl | —CH₂—CH₂— | Cl | H | N | NMR spectrum FIG. 6 |
| I-13 | 4-Cl-phenyl | —CH=CH— | —SCH₃ | H | N | NMR spectrum FIG. 7 |
| I-14 | 4-Cl-phenyl | —CH=CH— (trans) | —S—phenyl | H | N | NMR spectrum FIG. 8 |
| I-15 | 4-Cl-phenyl | —CH=CH— (cis) | —S—phenyl | H | N | NMR spectrum FIG. 9 |

TABLE 3-continued

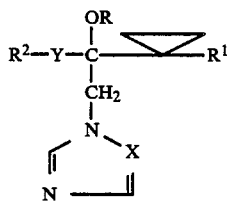
(I)

| Compound No. | R² | Y | R¹ | R | X | Characterization by |
|---|---|---|---|---|---|---|
| I-16 | 3,4-dichlorophenyl | —CH=CH— | —SC₂H₅ | H | N | NMR spectrum FIG. 10 |
| I-17 | 4-chlorophenyl | —CH₂—C(CH₃)₂—CH₂—CH₂— | Cl | H | N | NMR spectrum FIG. 11 |
| I-18 | 4-trifluoromethylphenyl | —CH₂—CH₂— | Cl | H | N | NMR spectrum FIG. 12 |
| I-19 | 2-chlorophenyl | —CH₂—CH₂— | Cl | H | N | m.p.: 100° C. |
| I-20 | 4-methylphenyl | —CH₂—CH₂— | Cl | H | N | m.p.: 118° C. |
| I-21 | 4-bromophenyl | —CH₂—CH₂— | Cl | H | N | m.p.: 132° C. |
| I-22 | 2,4-dichlorophenyl | —CH₂—CH₂— | Cl | H | N | m.p.: 108° C. |
| I-23 | phenyl | —CH₂—CH₂— | Cl | H | N | m.p.: 94° C. |
| I-24 | 4-trifluoromethoxyphenyl | —CH₂—CH₂— | Cl | H | N | NMR spectrum FIG. 13 |
| I-25 | 4-biphenylyl | —CH₂—CH₂— | Cl | H | N | m.p.: 128° C. |

TABLE 3-continued

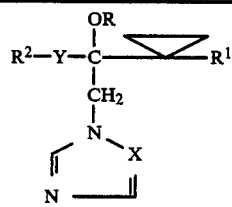
(I)

| Compound No. | $R^2$ | Y | $R^1$ | R | X | Characterization by |
|---|---|---|---|---|---|---|
| I-26 | 3-Br-4-F-phenyl | —CH$_2$—CH$_2$— | Cl | H | N | NMR spectrum FIG. 14 |
| I-27 | 3-CF$_3$-phenyl | —CH$_2$—CH$_2$— | Cl | H | N | NMR spectrum FIG. 15 |
| I-28 | 4-CH$_3$-phenyl | —CH=CH— | Cl | H | N | m.p.: 106° C. |
| I-29 | 2,4-diCl-phenyl | —CH=CH— | Cl | H | N | m.p.: 112° C. |
| I-30 | 4-Br-phenyl | —CH=CH— | Cl | H | N | m.p.: 130° C. |
| I-31 | 2-Cl-phenyl | —CH=CH— | Cl | H | N | m.p.: 133° C. |
| I-32 | phenyl | —CH=CH— | Cl | H | N | m.p.: 90° C. |
| I-33 | 4-CF$_3$O-phenyl | —CH=CH— | Cl | H | N | m.p.: 67° C. |
| I-34 | 3-Br-4-F-phenyl | —CH=CH— | Cl | H | N | m.p.: 126° C. |
| I-35 | 3-CF$_3$-phenyl | —CH=CH— | Cl | H | N | NMR spectrum FIG. 16 |

TABLE 3-continued

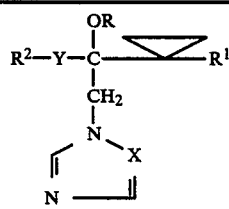
(I)

| Compound No. | R² | Y | R¹ | R | X | Characterization by |
|---|---|---|---|---|---|---|
| I-36 | 3,4-dichlorophenyl | —CH=CH— | Cl | H | N | NMR spectrum FIG. 17 |
| I-37 | 3-fluorophenyl | —CH=CH— | Cl | H | N | NMR spectrum FIG. 18 |
| I-38 | (CH₃)₃C— | —CH=CH— | Cl | H | N | m.p.: 74° C. |
| I-39 | cyclohexyl | —CH=CH— | Cl | H | N | m.p.: 95° C. |
| I-40 | cyclohexyl | —CH₂—CH₂— | Cl | H | N | m.p.: 67° C. |
| I-41 | 4-(CF₃S)phenyl | —CH=CH— | Cl | H | N | $R_f = 0.32$ (CH₂Cl₂/acetic acid = 4:1) |
| I-42 | 4-chloro-2-fluorophenyl | —CH=CH— | Cl | H | N | m.p: 92° C. |
| I-43 | 2-chloro-6-fluorophenyl | —CH=CH— | Cl | H | N | m.p: 112° C. |
| I-44 | 3-fluorophenyl | —CH₂—CH₂— | Cl | H | N | m.p = 0,34 (CH₂Cl₂/acetic acid ester = 4:1) |
| I-45 | 3-fluoro-2-chlorophenyl | —CH=CH— | Cl | H | N | m.p: 112° C. |

TABLE 3-continued

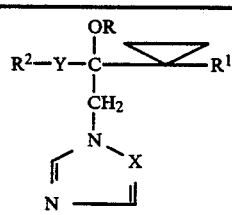
(I)

| Compound No. | R² | Y | R¹ | R | X | Characterization by |
|---|---|---|---|---|---|---|
| I-46 | 3,4-dichlorophenyl | —CH₂—CH₂— | Cl | H | N | m.p: 137° C. |
| I-47 | 2-naphthyl | —CH=CH— | Cl | H | N | m.p: 114–116° C. |
| I-48 | 2-chloro-3-fluorophenyl | —CH₂—CH₂— | Cl | H | N | m.p: 84° C. |
| I-49 | 2-chloro-6-fluorophenyl | —CH₂—CH₂— | Cl | H | N | m.p: 72° C. |
| I-50 | 4-(CF₃S)phenyl | —CH₂—CH₂— | Cl | H | N | m.p: 88° C. |
| I-51 | 4-O₂N-phenyl | —CH₂—CH₂— | Cl | H | N | m.p: 105° C. |
| I-52 | 4-Cl-phenyl | —CH=CH— | Cl | H | N | m.p: 122° C. |
| I-53 | 4-CH₃O-phenyl | —CH₂—CH₂— | Cl | H | N | m.p: 90° C. |
| I-54 | 2-naphthyl | —CH₂—CH₂— | Cl | H | N | m.p: 134° C. |
| I-55 | 2,2-difluoro-1,3-benzodioxol-5-yl | —CH=CH— | Cl | H | N | Oil |

TABLE 3-continued

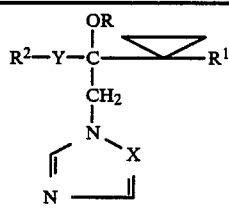
(I)

| Compound No. | R² | Y | R¹ | R | X | Characterization by |
|---|---|---|---|---|---|---|
| I-56 | 1-naphthyl | —CH₂—CH₂— | Cl | H | N | m.p: 102° C. |
| I-57 | 4-Cl, 2-F-phenyl | —CH₂—CH₂— | Cl | H | N | m.p: 112° C. |
| I-58 | 4-Cl-phenyl | —C≡C— | Cl | H | N | m.p: 112° C. |
| I-59 | 2-Cl-phenyl | —C≡C— | Cl | H | N | Oil |
| I-60 | phenyl | —C≡C— | Cl | H | N | m.p: 116–118° C. |
| I-61 | 4-F₃CO-phenyl | —CH₂—CH₂— | 4-Cl-phenyl | H | N | m.p: 132° C. |
| I-62 | 4-Cl-phenyl | —CH₂—CH₂— | 4-Cl-phenyl | H | N | m.p: 123° C. |
| I-63 | 4-F₃CO-phenyl | —CH=CH— | 4-Cl-phenyl | H | N | m.p: 82° C. |
| I-63 | 4-Cl-phenyl | —CH=CH— | 4-Cl-phenyl | H | N | m.p: 146° C. |

The compounds of the formulae given below were used as comparison substances in the following use examples:

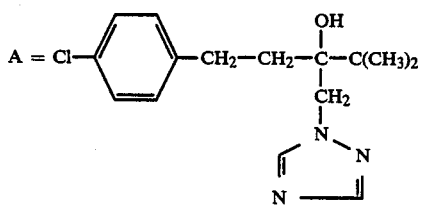

(known from EP-OS (European Published Specification) 0,040,345)

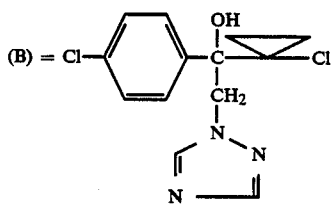

(known from EP-OS (European Published Specification) 0,180,136)

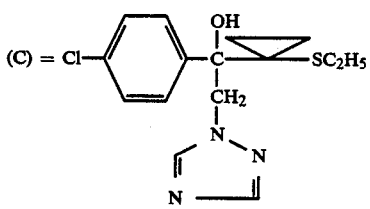

(known from EP-OS (European Published Specification) 0,180,136)

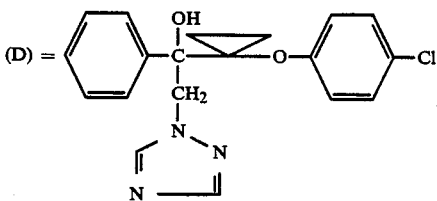

(known from EP-OS (European Published Specification) 0,180,136).

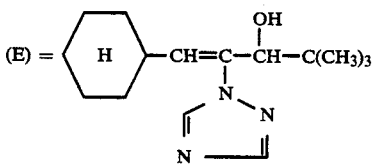

(known from EP-OS 0 015 387)

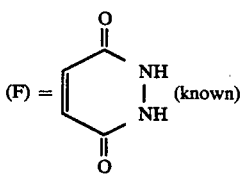

-continued (G): $Cl-CH_2-CH_2-\overset{\oplus}{N}(CH_3)_3 \; Cl^{\ominus}$(known)

EXAMPLE A

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compound (I-1) according to the invention shows a better activity than the comparison substances (A) and (B).

EXAMPLE B

Cochliobolus sativus test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on the plants are sprayed with a conidia suspension of Cochliobolus sativus. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, the compounds (I-1) and (I-5) according to the invention show a better activity than the comparison substances (C) and (D).

EXAMPLE C

GROWTH OF WHEAT

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Wheat plants are grown in a greenhouse to the 2-leaf stage. At this stage, the plants are sprayed with the preparations of active compound until dripping wet. After 2 weeks, the additional growth is measured on all plants and the growth in per cent of the additional growth of the control plants is calculated. 100% denotes a growth corresponding to that of the control plants and 0% means that the growth has stopped completely, Values above 100% characterize promotion of growth.

In this test, compound (I-38) according to the invention shows a markedly better activity than the comparison substance (E).

EXAMPLE D
GROWTH OF BARLEY

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Barley plants are grown in a greenhouse to the 2-leaf stage. In this stage, the plants are sprayed with the preparations of active compound until dripping wet. After 2 weeks, the additional growth is measured on all plants and the growth in per cent of the additional growth of the control plants is calculated. 100% denotes a growth corresponding to that of the control plants and 0% means that the growth has stopped completely. Values above 100% characterize promotion of growth.

In this test, compound (I-38) according to the invention shows a very good growth-inhibiting action.

EXAMPLE E
GROWTH OF GRASS (Festuca Pratensis)

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Grass plants (Festuca pratensis) are grown in a greenhouse up to a height in growth of 5 cm. In this stage the plants are sprayed with the preparations of active compound until dripping wet. After 2 weeks, the additional growth of the plants is measured and the growth in per cent of the growth of the control plants is calculated. 100% growth denotes a growth corresponding to that of the control plants and 0% denotes that growth has stopped. Values above 100% characterise a promotion of growth.

In this test, the compound (I-38) according to the invention shows a markedly better growth inhibiting activity than the comparison substances (F) and (E).

EXAMPLE F
GROWTH OF RYE

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Rye plants are grown in a greenhouse to the 2-leaf stage. At this stage, the plants are sprayed with the preparations of active compound until dripping wet. After 2 weeks, the additional growth is measured on all plants and the growth in per cent of the additional growth of the control plants is calculated. 100% denotes a growth corresponding to that of the control plants and 0% denotes that the growth has stopped completely. Values above 100% characterize promotion of growth.

In this test, compound (I-38) according to the invention shows a markedly better growth-inhibiting activity than the comparison substance (G).

It is understood that the specification and examples are illustrative but not limitative of the present invention and that other embodiments within the spirit and scope of the invention will suggest themselves to those skilled in the art.

We claim:

1. A hydroxyalkyl-azolyl derivative of the formula

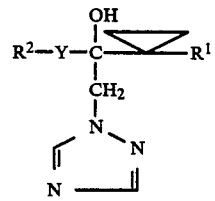

in which $R^1$ is fluorine, chlorine, bromine or phenyl which is optionally substituted by chlorine, or is dichloro-substituted phenoxy, $R^2$ is alkyl with 1 to 4 carbon atoms, which is optionally mono- or di-substituted by methoxy, or is cycloalkyl having 3 to 7 carbon atoms, which is optionally mono-substituted by methyl, or is naphthyl, or the radical of the formula

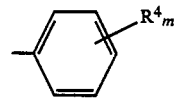

wherein $R^4$ is fluorine, chlorine, bromine, methyl, ethyl, isopropyl, tert.-butyl, methoxy, trifluoromethyl, trifluoromethoxy, trifluoromethylthio, phenyl, phenoxy or nitro, and m is 0, 1, 2 or 3, or $R^2$ is the radical of the formula

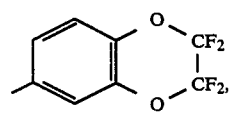

and

Y represents the groupings —CH$_2$—CH$_2$—, —CH═CH—, —C≡C— or

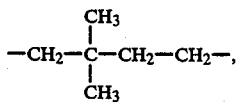

or an addition product thereof with an acid or metal salt.

2. A compound or addition product thereof according to claim 1, in which $R^1$ is fluorine, chlorine, bromine or phenyl.

3. A compound or addition product thereof according to claim 1, in which $R^1$ is chlorine.

4. A compound or addition product thereof according to claim 1, in which $R^1$ is phenyl.

5. A compound according to claim 1, wherein such compound is 2-(1-chlorocyclopropyl)-4-(4-chlorophenyl)-1-(1,2,4-triazol-1-yl)-butan-2-ol of the formula

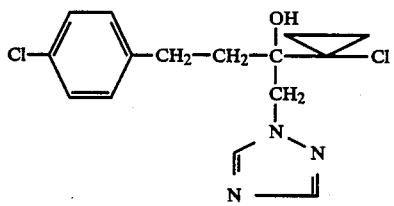

or an addition product thereof with an acid or metal salt.

6. A compound according to claim 1, wherein such compound is 4-(4-chlorophenyl)-2-[1-(2,4-dichlorophenoxy)cyclopropyl]-1-(1,2,4-triazol-1-yl)-butan-2-ol of the formula

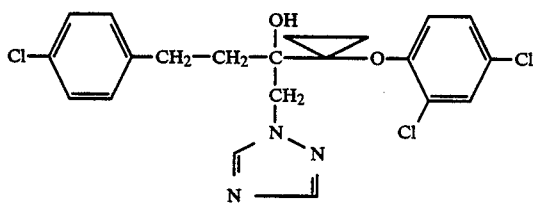

or an addition product thereof with an acid or metal salt.

7. A compound according to claim 1, wherein such compound is 2-(1-chlorocyclopropyl)-5,5-dimethyl-1-(1,2,4-triazol-1-yl)-hex-3-en-2-ol of the formula

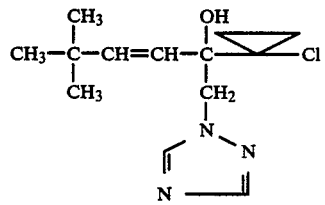

or an addition product thereof with an acid or metal salt.

8. A compound according to claim 1, wherein such compound is 2-(1-chlorocyclopropyl)-4-(4-chlorophenyl)-1-(1,2,4-triazol-1-yl)-but-3-yn-2-ol of the formula

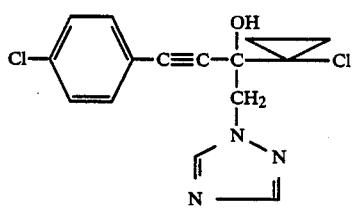

or an addition product thereof with an acid or metal salt.

9. A fungicidal or plant growth regulating composition comprising an amount effective therefor of a compound or addition product according to claim 1 and an inert diluent.

10. A method of combating fungi which comprises applying to such fungi or to a fungus habitat a fungicidally effective amount of a compound or addition product according to claim 1.

11. The method according to claim 10, wherein such compound is
2-(1-chlorocyclopropyl)-4-(4-chlorophenyl)-1-(1,2,4-triazol-1-yl)-butan-2-ol,
4-(4-chlorophenyl)-2-[1-(2,4-dichlorophenoxy)cyclopropyl]-1-(1,2,4-triazol-1-yl)-butan-2-ol,
2-(1-chlorocyclopropyl)-5,5-dimethyl-1-(1,2,4-triazol-1-yl)-hex-3-en-2-ol or
2-(1-chlorocyclopropyl)-4-(4-chlorophenyl)-1-(1,2,4-triazol-1-yl)-but-3-yn-2-ol,
or an addition product thereof with an acid or metal salt.

12. A method of regulating the growth of plants which comprises applying to such plants or to a locus in which such plants are growing or are to be grown an amount effective therefor of a compound or addition product according to claim 1.

13. The method according to claim 12, wherein such compound is
2-(1-chlorocyclopropyl)-4-(4-chlorophenyl)-1-(1,2,4-triazol-1-yl)-butan-2-ol,
4-(4-chlorophenyl)-2-[1-(2,4-dichlorophenoxy)cyclopropyl]-1-(1,2,4-triazol-1-yl)-butan-2-ol,
2-(1-chlorocyclopropyl)-5,5-dimethyl-1-(1,2,4-triazol-1-yl)-hex-3-en-2-ol or
2-(1-chlorocyclopropyl)-4-(4-chlorophenyl)-1-(1,2,4-triazol-1-yl)-but-3-yn-2-ol,
or an addition product thereof with an acid or metal salt.

* * * * *